United States Patent
Wang

(10) Patent No.: US 7,534,457 B2
(45) Date of Patent: May 19, 2009

(54) HEMOSTATIC MISTURA OF IPOMOEA BALATAS LEAVES, METHODS OF PREPARATION AND USE THEREOF

(75) Inventor: Xinting Wang, 3-2-602 Yiyuan Anhuibeili, Chaoyang District, Beijing (CN) 100101

(73) Assignee: Xinting Wang, Beijing (CN)

( * ) Notice: Subject to any disclaimer, the term of this patent is extended or adjusted under 35 U.S.C. 154(b) by 0 days.

(21) Appl. No.: 11/725,081

(22) Filed: Mar. 16, 2007

(65) Prior Publication Data

US 2007/0160701 A1 Jul. 12, 2007

Related U.S. Application Data

(63) Continuation of application No. PCT/CN2004/001181, filed on Oct. 18, 2004.

(51) Int. Cl.
*A61K 36/00* (2006.01)
(52) U.S. Cl. ...................................... 424/773
(58) Field of Classification Search ........................ None
See application file for complete search history.

(56) References Cited

U.S. PATENT DOCUMENTS

2006/0034984 A1* 2/2006 Baydo et al. ................ 426/250

FOREIGN PATENT DOCUMENTS

JP 0199651 A * 9/2006

OTHER PUBLICATIONS

Li et al, Effect of Polysaccharide from the leaves of Ipomoea Batatas Lam on platelet count and its action mechanism, Beijing Yike Daxue Xuebao (1993), vol. 25 (4), pp. 261-263.*
International Search Report and Written Opinion issued Apr. 14, 2005, in related Chinese Patent Application No. PCT/CN2004/001181, with English translation (6 pages).
PCT International Preliminary Report on Patentability dated Dec. 31, 2006, in related Chinese Patent Application No. PCT/CN2004/001181, with English translation (10 pages).

* cited by examiner

*Primary Examiner*—Christopher R Tate
*Assistant Examiner*—Deborah A. Davis
(74) *Attorney, Agent, or Firm*—Osha • Liang LLP

(57) ABSTRACT

Jinshuye styptic compositions, preparation methods and applications thereof are disclosed. A Jinshuye styptic composition is a plant preparation made by extracting leaf and stem of sweet potato (*Ipomoea batatas*, Jinshu), by purification and water extraction to obtain polysaccharides as active ingredients from the raw materials. Such a composition has the effects of invigorating spleen, cooling blood and stopping bleeding. Such a composition can be used for treatment of ITP, thrombocytopenia caused by radiotherapy and chemotherapy of tumors, and skin purpura caused by other factors.

12 Claims, No Drawings

HEMOSTATIC MISTURA OF IPOMOEA BALATAS LEAVES, METHODS OF PREPARATION AND USE THEREOF

CROSS-REFERNCE TO RELATED APPLICATIONS

This is a Continuation-In-Part of Application No. PCT/CN2004/001181, filed on Oct. 18, 2004, which designates the U.S. and claims priority of Chinese Patent Application No. 200410077900.2, filed on Sep. 16, 2004.

FIELD OF THE INVENTION

The present invention relates to a styptic composition, its preparation method and application, specifically Jinshuye styptic composition made by extraction and purification of a single plant for treating thrombocytopenia and regulating immunity, its preparation method and application.

DESCRIPTION OF THE RELATED ART

Idiopathic thrombocytopenic purpura (ITP) is a common hemorrhagic disease caused by increase of platelet destruction, which is also called immunologic thrombocytopenic purpura since it is related to autoimmunity. ITP has an annual incidence of 40-100/0.1 million, and the new incidence is over 0.8 million annually for China with a population of 1.3 billion. The patients of the disease are mostly children and youth (mainly female youth). The symptoms of the disease include spontaneous hemorrhage of skin and mucous membrane, thrombocytopenia, prolonged bleeding time, and increased capillary fragility. The disease may even cause intracranial hemorrhage or death. The cause of the disease is not totally clear, and it is generally thought to be that increase of serum antiplatelet antibody influences platelet formation and accelerates platelet destruction, resulting in significant reduction of platelet count. ITP is clinically common, and is a blood disease which is hard to cure.

At present, ITP is clinically treated mainly with adrenocortical hormones and secondly with immunosuppressant. Although such drugs can increase the platelet count in the short term, they have counter indications and will show severe adverse effects after administration for more than one week, which include hypertension, hyperglycemia, complicated infection, emotional disturbance, obesity, glaucoma, cataract, femur head necrosis, and after long term administration thrombocytopenia for adrenocortical hormones, and bone marrow suppression, alopecia, hepatic lesion and risk of viral infection if using gamma globulin for immunosuppression. Splenectomy may be clinically adopted if the therapy with adrenocortical hormones and immunosuppressant such as gamma globulin turns out to be ineffective. Splenectomy is usually not recommendable, because it causes big trauma, the patient will lose the biggest lymphatic organ in the body for ever, and the recurrence rate of ITP is high after the operation.

According to traditional Chinese medicine, deficiency of spleen-yin is the main cause of ITP. Spleen is responsible for maintaining normal function of digestion, and plays a key role in circulation and regeneration of qi and blood. Patients of ITP suffers from intrinsic "heat" generated by yin deficiency, excessive "heat" in turn interferes with blood circulation to cause extravasation of blood and induce hemorrhage, and purpura occurs when the blood stagnates under the skin.

Malignant tumors of human are common and frequently occurring diseases. According to statistics, the number of new tumor patients in China alone is two million annually. According to report of world health organization in 2001, the new tumor incidence was ten million over the world annually. Combined therapy of tumors is clinically recommended at present, for which radiotherapy and chemotherapy are the two methods most frequently adopted. Radiation and chemotherapeutic drugs cause severe harm to the normal tissues and organs during the process of killing cancer cells, especially to the bone marrow hematopoietic system and immune system, resulting in bone marrow suppression, leukopenia and thrombocytopenia. The severe consequence of leukopenia has been effectively controlled with the clinical application of granulocyte growth factor. While there is no better resort than infusion of platelet suspension for treating hemorrhage caused by thrombocytopenia at present, infusion of platelet suspension incurs high risk of infection by viruses. The patient should get fully prepared for the next treatment course of radiotherapy or chemotherapy in an interval of 20 days, which means the hemogram and platelet count must return to the normal ranges in the period. Jinshuye styptic composition has good effect in increasing the platelet count in the interval of radiotherapy or chemotherapy, and can alleviate the side effect of radiotherapy and chemotherapy.

It can be noted that the drugs and treatment methods for thrombocytopenia need immediate improvement due to the mentioned shortcomings. Professionals, research institutes, and business owners in the fields of medicine and pharmacology at home and abroad are all keen on finding methods to overcome the shortcomings, yet no applicable drug has been developed and other products lack the desired properties to serve the purpose.

With the mentioned shortcomings of existing drugs in mind, the inventor of the present invention carried out active research, fully utilizing the expertise and work experience obtained in the nine years of drug design and production, in hope of inventing a new styptic composition with improved application compared with existing drugs and treatment methods. The present invention with great applicability was finally accomplished after unremitting study, design, experiment, sample production and modification.

DETAILED DESCRIPTION OF THE INVENTION

It is one object of the present invention to overcome the shortcomings of existing drugs and treatment methods for thrombocytopenia by providing a new Jinshuye styptic composition and its application. The technical problems to be solved include avoiding the adverse side effects and counter indications of the composition in the process of increasing platelet, so as to improve its compliance, make it suitable for long term administration, improve its compliance and improve its industrial applicability.

It is another object of the present invention to provide the preparation method and application of the Jinshuye styptic composition. The technical problems to be solved include using the drug to improve the life quality of patients of autoimmune disease and tumor patients undergoing radiotherapy and chemotherapy, so as to improve its practicability and industrial applicability.

The techniques for realizing the objects of the present invention and solving the technical problems are disclosed below. The inventive Jinshuye styptic composition for treating the hemorrhagic disease of thrombocytopenia is prepared from a single plant belonging to the family of Convolvulaceae (sweet potato), by extracting leaves or leaves with stems with an alcohol (e.g., ethanol), drying (e.g., air drying), removing chlorophyll, extracting with water, filtering (e.g., by vacuum filtration), concentrating the filtrate (for example, with a triple effect evaporator at a temperature of 65-85° C., pressure of 0.04-0.06 MPa, and vapor pressure of 0.01-0.06 MPa) to obtain a concentrate with a density of about 1.0-1.3 g/mL, filtering, packaging and sterilizing.

The techniques for realizing the objects of the present invention and solving the technical problems are further disclosed below.

The aforementioned sweet potato belonging to the family of Convolvulaceae is *Ipomoea batatas* (Jinshu). The leaf or leaves of *Ipomoea batatas* will be referred to as "Jinshuye."

The aforementioned Jinshuye styptic composition may be available in the dosage form of capsule, tablet, granule, injection, pill, powder, syrup, solution, unguent, paste, ointment, tea preparation, aerosol or spray.

The techniques for realizing the objects of the present invention and solving the technical problems may be described as follows. An exemplary preparation method of Jinshuye styptic composition may comprise the steps of (1) pulverizing the raw materials into powders; (2) extracting the powders with alcohol to obtain an alcohol extract and a medicinal residue; (3) drying and extracting the medicinal residue with water to obtain an aqueous extract; (4) mixing the extracts, filtering, separating by centrifugation to give supernatant, and concentrating the supernatant; and (5) optionally, further filtering the concentrate, packaging and sterilizing.

The techniques for realizing the objects of the present invention and solving the technical problems can be further described as below.

The aforementioned Jinshuye styptic composition and its preparation method comprise alcohol extraction at 0-50° C. for 5-15 h.

The aforementioned Jinshuye styptic composition and its preparation method comprise alcohol extraction with a 50-90% (by weight) ethanol solution.

The aforementioned Jinshuye styptic composition and its preparation method comprise alcohol extraction by use of a solvent with a volume 4-15 times that of the raw materials.

The aforementioned Jinshuye styptic composition and its preparation method comprise water extraction at 45-95° C. for 2-7 h with a volume of water 5-15 times that of the raw materials.

The aforementioned Jinshuye styptic composition and its preparation method comprise centrifugation at 4,000-30,000 rpm, and concentration of the supernatant to obtain a concentrate with density of about 0.98-1.09 g/mL (40-75° C.).

The aforementioned Jinshuye styptic composition and its preparation method comprise centrifugation at 16,000 rpm.

The inventive Jinshuye styptic composition can be used in medicinal preparation for treating idiopathic thrombocytopenic purpura.

The inventive Jinshuye styptic composition can be used in medicinal preparation for adjuvant therapy of thrombocytopenia induced by radiotherapy and chemotherapy of tumors and skin purpura caused by other factors.

The aforementioned Jinshuye styptic composition has the main functions of invigorating spleen and qi, cooling blood and stopping bleeding. It can also be used in treatment of ITP with spleen deficiency caused by weakness of qi and with heat in blood, thrombocytopenia induced by radiotherapy and chemotherapy of tumors, skin purpura caused by other factors, and related diseases.

The aforementioned Jinshuye styptic composition is in form of a mixture, and may also be available in the dosage forms such as capsule, tablet, granule, injection, pill, powder, syrup, unguent, rubber plaster, ointment, tea preparation, aerosol and spray.

The aforementioned Jinshuye styptic composition is preferably administered with an empty stomach about half an hour before meals for 2-3 times a day, about 10 mL for children and about 20-30 mL for adults each time. The patients with severe hemorrhage and platelet count below 50,000/microliter may double the dose or follow doctor's prescription.

Toxicity tests for the present invention are described as below.

1. Acute Toxicity Test

Test Materials:

Animals were provided by Laboratory Animal Center, Institute of Genetics, Chinese Academy of Sciences, including 40 Kunming mice (20 males and 20 females) with body weights of 18.50±1.00 g.

The drug was a Jinshuye styptic composition of the invention (1.06 g crude drug/mL).

Test Method:

The mice were administered the drug twice a day by intragastric administration with a 16 gauge needle after starvation for 12 h, with a single dose of 0.6 mL (1.06 g crude drug/mL) for 20 g body weight (cumulative dose of 63.6 g crude drug/Kg). The control group was administered with water. The mice were observed and their body weights were obtained each day for 7 days on end. The body weight gain is displayed in Table 1.

TABLE 1

Body weight gain of mice (mean ± SD)

| grouping | n | Control group | Experimental group |
|---|---|---|---|
| Before administration | 20 | 18.15 ± 0.88 | 18.50 ± 1.00 |
| 1 day after administration | 20 | 19.75 ± 1.12 | 19.30 ± 1.13 |
| 2 days after administration | 20 | 21.50 ± 1.50 | 20.50 ± 1.70 |
| 3 days after administration | 20 | 21.90 ± 1.70 | 21.10 ± 1.97 |
| 4 days after administration | 20 | 22.75 ± 1.94 | 21.75 ± 2.05 |
| 5 days after administration | 20 | 23.25 ± 2.63 | 22.40 ± 2.39 |
| 6 days after administration | 20 | 23.60 ± 3.00 | 23.00 ± 2.85 |
| 7 days after administration | 20 | 24.15 ± 3.39 | 23.35 ± 3.36 |

Test Results:

The mice were observed and their body weights were obtained each day for 7 days on end after administration of the inventive composition. No obvious adverse effect or death for the experimental group of 20 mice was observed. The mice in the experimental group had an increased body weight of 23.35±3.36 g one week after administration, good mental state, white and lustrous fur, and normal urine and stool. The largest tolerated dose for mice in intragastric administration is 63.6 g crude drug/Kg, which is 259.5 times the clinical dose.

2. Long Term Toxicity Test on a Large Scale

Test Materials:

Animals were provided by Institute of Laboratory Animal, Chinese Academy of Sciences, including 80 Wistar rats (half being male and half being female) with body weight of 90.05±6.25 g.

The drug was the inventive Jinshuye styptic composition (1.06 g crude drug/mL).

Test Method:

The rats were randomly divided into four groups, each group comprising 10 male rats and 10 female rats. The control group was administered water with the same volume as the drug. The experimental groups were administered Jinshuye styptic composition by intragastric administration for three months on end, at a dose of 3.06 g crude drug/Kg, 6.13 g crude drug/Kg or 12.26 g crude drug/Kg. Each week the rats were weighed and the dose was adjusted accordingly. The feed was weighed for four days on end in the last week of each month during the three month period for calculation of the mean daily feed intake of each rat.

Test Results:

No adverse effect was observed during administration or in the two weeks after drug withdrawal for the experimental groups which were administered Jinshuye styptic composition for three months on end by intragastric administration at a dose of 3.06 g crude drug/Kg (12.5 times the clinical dose), 6.13 g crude drug/Kg (25 times the clinical dose) or 12.26 g crude drug/Kg (50 times the clinical dose). Their physiological indexes fell into the normal ranges, and no pathological change due to toxicity was observed in pathological examination.

The present invention has obvious advantages and benefits when compared with prior arts. It can be noted in the above description that the main techniques for realization of the objects of the present invention can be summarized as below.

The techniques of the present invention, based on achievements in contemporary pharmacology, pharmacodynamics, toxicology, preparation method, and clinical trials and with reference to pathogenetic understanding and treatment principles of hemorrhagic diseases in Chinese medicine, include selecting a single medicinal plant with effects in invigorating spleen and qi, cooling blood and stopping bleeding and extracting the active ingredients of the plant following the theories in life science and traditional Chinese medicine and utilizing the modern preparation method, so as to improve its effects in restoring the function of megakaryocyte, improving hematopoietic function, restoring platelet count to the normal range, promoting platelet formation, and regulating the immune function. The composition displays good therapeutic effect after several treatment courses, and can gradually help patients with dependency on hormone drugs to get rid of the side effects caused by hormone drugs. Even administration of Jinshuye styptic composition alone can display desired therapeutic effect.

The present invention provides the preparation method and application of Jinshuye styptic composition made from a single plant. The composition is prepared by purification of leaf and stem of *Ipomoea batatas* and water extraction to obtain the active ingredients such as polysaccharides and flavones. The composition has the effects of invigorating spleen and qi, cooling blood and stopping bleeding, and can be used for treating ITP and thrombocytopenia induced by radiotherapy and chemotherapy of tumors. It has the advantages of simple formula, good therapeutic effect, no adverse side effect, no counter indications, suitability for long term administration, and good compliance. Clinically the inventive composition can serve as a new means of treating thrombocytopenia, and is a good substitution of drugs containing hormone or immunosuppressant.

One important feature of the inventive composition is that it contains abundant active ingredients and rich nutrition, such as polysaccharides as the major active ingredients, vitamins, more than ten amino acids and microelements. The mentioned ingredients existing at desired ratio in the composition can influence and complement one another in a desired manner, which greatly improves the therapeutic effects of the composition.

Clinical application of a composition of the invention shows that it has the following advantages.

A composition of the invention has significant effects in cooling blood, stopping bleeding, increasing platelet, and regulating immunity, with a total effective rate above 80%.

A composition of the invention has no adverse effect or counter indications in the process of increasing platelet. It can be applied for improving the life quality of thrombocytopenia patients and tumor patients undergoing radiotherapy and chemotherapy, even including women, children, the elderly, and patients with liver diseases, kidney diseases or cardiovascular diseases.

The toxicity tests have shown that a composition of the invention has no toxicity.

To sum up, a composition of a special formula of the invention is suitable for a wide application, because it has no adverse side effect or counter indications in the process of increasing platelet and can improve the life quality of thrombocytopenia patients and tumor patients undergoing radiotherapy and chemotherapy. As stated above, compositions of the invention have multiple advantages, good applicability, and significant improvement in formula and function. Moreover, no products with similar formula or preparation method have been publicly disclosed or utilized. The compositions of the invention have good safety, good therapeutic effect, convenient and wide application, and multiple functions when compared with drugs that are presently used clinically. Embodiments of the invention provide a new way for clinical treatment of ITP and thrombocytopenia. In a word, embodiments of the present invention have novelty, inventiveness and practical applicability for medicinal industry and on the international market.

The present invention is further illustrated by but not limited to the following embodiments.

MOST PREFERRED EMBODIMENTS OF THE INVENTION

For further illustration of the techniques for realization of the objects of the present invention and its effects, detailed description of the embodiments and effects of the inventive Jinshuye styptic composition, its preparation method and application are given below with reference to the figures and preferred embodiments.

Embodiment 1

This embodiment is provided to illustrate a preparation method of the present invention.

A preparation method of the invention may comprise: taking 100 g of dried stem and leaf of *Ipomoea batatas*, removing impurities, pulverizing, putting in a common container, adding 70% ethanol 1,400 mL, soaking at 25° C. for 10 h, filtering, air drying the residue and removing chlorophyll, transferring the residue into a common container, adding purified water 1,000 mL, soaking at 70° C. for 4 h, repeating soaking one more time, mixing the extracts, filtering, centrifuging the filtrate at 16,000 rpm to obtain an extract with a density over 1.0 g/mL and a temperature of 2-70° C., concentrating with a triple effect evaporator to obtain a concentrate with a relative density of 1.20, adding preservative into the concentrate, filtering, packaging and sterilizing to obtain mixture.

The concentrating procedures using a triple effect evaporator may be performed under the following conditions: a first evaporation step with a pressure of 0.02 MPa, a temperature of 85° C., a vapor pressure of 0.01 MPa, and gas consumption of 625 Kg/h; a second evaporation step with a temperature of 75° C., a pressure of 0.05 MPa, and a vapor pressure of 0.03 MPa; and a third evaporation step with a temperature of 60° C., a pressure of 0.08 MPa, a vapor pressure of 0.06 MPa, and gas consumption of 625 Kg/h.

The preparation method described above illustrates a preferred method that has the advantages of shortened process and improved protection of the effective ingredients due to adoption of vacuum concentration under relatively low temperature, which is very suitable for concentration of temperature sensitive substances. One of ordinary skill in the art would appreciate that other suitable methods (such a lyophilization) may also be used.

Embodiment 2

This embodiment describes the good therapeutic effects of the invention in clinical practice.

A girl patient of 14 was diagnosed with ITP at the age of seven. She had been administered hormone drugs but achieved no desired therapeutic effect. She had intracranial hemorrhage twice, the right eye was nearly blind due to adverse side effect of the hormone therapy, and the intraocular pressure was above 60. She also suffered from obesity and headache. The girl started to take a styptic composition of the invention beginning on May 29, 2004 with a dose of 10 mL each time, three times a day. She stopped taking hormone drugs on June 2, when her platelet count reached 44,000 (once 23,000). After one more week of administration of the styptic composition, her platelet count reached 67,000. On Jun. 14, 2004, her health examination in Beijing Tongren Hospital showed her intraocular pressure was normal, and there was no sign of headache. Her right eyesight increased to 0.2 from 0.01, and left eyesight was 1.2.

A male patient of New Zealand nationality was diagnosed with ITP four years before administration of a styptic composition of the invention. He had been hospitalized several times and took hormone drugs among others. His platelet count was only 5,000. His platelet count reached 139,000 after one treatment course with the styptic composition, and 168,000 after two courses. He recovered after several such treatment courses.

A female patient of 58 was diagnosed with non-Hodgkin lymphoma of stage IVB (diffuse small non-cleaved cell lymphoma) with complication of immunologic thrombocytopenic purpura six years before treatment with a styptic composition of the invention. She was subjected to regular chemotherapy. Before hospitalization her platelet count stayed below $10 \times 10^9$/L, and she suffered from occasional gingival bleeding. She took cyclosporine A and prednisone, but got no desired therapeutic effect, and, therefore, she had been off chemotherapy for over eight months. Medical examination before hospitalization showed that she had the symptoms of mild anemia, a number of ecchymoses, multiple swelling lymph nodes palpable at the cervical parts and armpits (up to $4 \times 3$ cm$^2$), and no palpable spleen or kidney. She was administered a styptic composition of the invention after hospitalization. Two weeks later, her platelet count reached $20 \times 10^9$/L and gingival bleeding stopped. Therefore, she continued the chemotherapy. During the chemotherapy period, she had no obvious hemorrhage and there was no need for any infusion of blood or platelet. In the interval of chemotherapy, she was administered the styptic composition and her platelet count was maintained at $(5-14) \times 10^9$/L. Now she is in tumor remission.

A male patient of 64 was diagnosed with esophageal cancer at Beijing Railway General Hospital. His platelet count dropped to 80,000 and bleeding and clotting time prolonged after two courses of chemotherapy. He started administration of a styptic composition of the invention during the third course of chemotherapy. Platelet count reached 180,000 and bleeding and clotting time became normal after one month of administration of the styptic composition. The patient is now in good mental state and has improved appetite.

As mentioned above, the basic idea of the present invention is to provide a novel drug for treating thrombocytopenia and related diseases. Other applicable embodiments with modification of the invention can readily be devised by technicians with basic knowledge in the technical fields of the invention and having the benefits of this description. Therefore, the scope of the protection, as defined by the attached claims, should cover all variations and modifications of the aforementioned technical features.

The present invention has been described with respect to the currently preferred embodiments disclosed above. These preferred embodiments are for illustration only, but not meant to limit the invention. Various changes and modifications, which can be easily devised by technician familiar with the fields of the invention having benefit of this description, are contemplated as being within the scope of the invention. All equivalent changes and modifications of the embodiments that carry the key technical features of the invention are to be considered within the scope of the invention.

INDUSTRIAL APPLICABILITY

The Jinshuye styptic compositions of the invention are plant preparations made by extracting the upper part leaf and stem of sweet potato (*Ipomoea batatas*) by purification and water extraction to obtain active ingredients including polysaccharides from the raw materials. The clinical trials have proved that the inventive drug has the effects of invigorating spleen and qi, cooling blood and stopping bleeding. The inventive composition can be used for treatment of ITP, thrombocytopenia caused by radiotherapy and chemotherapy of tumors, and skin purpura caused by other factors, and for alleviation of side effects of radiotherapy and chemotherapy. The present invention also provides the preparation method of the composition, which proves that the present invention has novelty and industrial applicability.

What is claimed is:

1. A styptic composition for treating a hemorrhagic disease of thrombocytopenia, comprising a product prepared by
   extracting leaves of sweet potato belonging to the family of Convolulaceae with an alcohol to produce an alcohol extract and a residue,
   drying the residue,
   removing chlorophyll from the residue,
   extracting the residue with water to produce an aqueous extract,
   combining the alcohol extract and the aqueous extract,
   filtering the combined extract, and
   concentrating the filtrate, wherein the styptic composition comprises polysaccharides as major active ingredients.

2. The styptic composition according to claim 1, wherein the sweet potato belonging to the family of Convolulaceae is *Ipomoea batatas* (Jinshu).

3. The styptic composition according to claim 1, wherein the styptic composition is in a dosage form of capsule, tablet, granule, injection, pill powder, syrup, solution, unguent, paste, ointment, tea preparation, aerosol, or spray.

4. A styptic composition prepared by a process having the following steps:
   (1) pulverizing *Ipomoea batatas* (Jinshuye) to obtain a powder;
   (2) extracting the powder with an alcohol to obtain an alcohol extract and a residue;
   (3) drying the residue;
   (4) removing chlorophyll from the residue, and extracting the residue with water to obtain an aqueous extract; and (5) combining the alcohol extract and the aqueous extract to produce a combined extract, filtering the combined extract, removing residues by centrifugation to obtain a supernatant, and concentrating the supernatant, to give a concentrate of the styptic composition having a relative density of about 1.0-1.3, wherein the styptic composition comprises polysaccharides as major active ingredients.

5. The styptic composition according to claim 4, wherein the alcohol extraction is performed at 0-50° C. for 5-15 h.

6. The styptic composition according to claim 4, wherein the alcohol extraction is performed with a 50-90% (by weight) ethanol solution.

7. The styptic composition according to claim 4, wherein the alcohol extraction is performed with a volume of alcohol 4-15 times that of the *Ipomoea batatas* leaves.

8. The styptic composition according to claim 4, wherein the water extraction is performed at 45-95° C. for 2-7 h with a volume of water 5-15 times that of the raw material.

9. The styptic composition according to claim 4, wherein the centrifugation is performed at 4,000-30,000 rpm, and concentrating the supernatant to obtain a concentrate with a density of 0.98-1.09 g/mL, as measured at 40-75° C.

10. The styptic composition according to claim 4, wherein the centrifugation is performed at 16,000 rpm.

11. A method for treating idiopathic thrombocytopenic purpura, comprising administering to a subject in need thereof the styptic composition according to claim 1.

12. A method for treating thrombocytopenia induced by radiotherapy and chemotherapy of tumors in a patient, comprising administering to the patient the styptic composition of claim 1.

* * * * *